(12) United States Patent
Kim et al.

(10) Patent No.: US 6,759,419 B2
(45) Date of Patent: Jul. 6, 2004

(54) PYRROLIDINONE DERIVATIVES, THEIR PREPARATION AND PHARMACEUTICAL COMPOSITION COMPRISING THE SAME

(75) Inventors: Youseung Kim, Seoul (KR); Soon Bang Kang, Uijeongbu-si (KR); Gyochang Keum, Seoul (KR); Min Seok Jang, Seoul (KR); Jae Yang Kong, Daejeon (KR); Dae Young Jeong, Daejeon (KR); Taeg-Su Jang, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/273,643

(22) Filed: Oct. 18, 2002

(65) Prior Publication Data

US 2003/0114491 A1 Jun. 19, 2003

(30) Foreign Application Priority Data

Oct. 27, 2001 (KR) .................................. 2001-66578

(51) Int. Cl.$^7$ ..................... A61K 31/445; C07D 413/14
(52) U.S. Cl. ................. 514/326; 514/340; 514/343; 514/378; 546/208; 546/209; 546/272.1; 548/247
(58) Field of Search ................. 514/326, 340, 514/343, 378; 546/208, 209, 272.1; 548/247

(56) References Cited

PUBLICATIONS

Wilbraham et al. "Organic and biological chemistry" S. Ill. Univ. press, p. 268–269 (1985).*
Yeh et al. "The 1,3–dipolar cycloadditions of . . . " CA 111:57640 (1989).*
Khadabadi et al. "Reactionso 4–acetyl–3–aryl . . . " CA 122:160560 (1995).*

* cited by examiner

Primary Examiner—Celia Chang
(74) Attorney, Agent, or Firm—Jones Day

(57) ABSTRACT

The present invention relates to substituted pyrrolidinone compounds of formula 1,

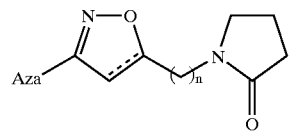

wherein n is 0 or 1; Aza is a heterocycle optionally substituted with $C_{1-4}$ alkyl, or $C_{1-4}$ alkyl substituted with a heterocycle, which represents a saturated or unsaturated five- or six-membered ring having nitrogen(s) as a heteroatom, which are muscarinic acetylcholine receptor agonists and useful as nootropics and therapeutic agents for cerebral neural diseases such as Alzheimer's disease; and pharmaceutically acceptable salts thereof; processes for the preparation thereof; and pharmaceutical compositions comprising these compounds or salts.

13 Claims, No Drawings

PYRROLIDINONE DERIVATIVES, THEIR PREPARATION AND PHARMACEUTICAL COMPOSITION COMPRISING THE SAME

FIELD OF THE INVENTION

The present invention relates to substituted pyrrolidinone compounds, which are muscarinic acetylcholine receptor agonists and thus useful as nootropics and therapeutic agents for cerebral neural diseases; and pharmaceutically acceptable salts thereof; processes for the preparation thereof; and pharmaceutical compositions comprising these compounds or salts.

BACKGROUND OF THE INVENTION

Due to the increase in the number of the elderly population, the number of geriatric diseases such as dementia have increased dramatically. Senile dementia, as represented by Alzheimer's disease, is a degenerative neural disease characterized by disorders of mental capacity including loss of memory, judgment and cognitive function. Patients suffering from Alzheimer's disease show up to 90% degeneration of pre-synapse muscarinic acetylcholine neurons of the basal ganglia, which project into the frontal lobe and hippocampus, both of which manage learning, association, consolidation, and cognitive function such as perception in the cerebrum. However, the post-synapse muscarinic neurons in the forebrain and hippocampus are relatively unchanged. These facts suggest the strategy of medicinal development based on cholinergic deficiency hypothesis, which focuses on the stimulation of post-synapse receptors [See; R. T. Bartus, et al. Science, 217, 408–417 (1982)].

Tacrine is an acetylcholine esterase inhibitor that enhances available acetylcholine, which was developed as an agent involved in cognitive function. However, Tacrine had adverse effects. Recently, Aricept (donepezil, Eisai America, Inc., 1996), Exelon (rivastigmine, Novartis Pharmaceuticals Corporation, 2000) and Reminyl (galantamine hydrobromide, Janssen Research, 2001) having enhanced efficacy were developed [See; W. Greenlee, et al. I1 Farmaco, 2001, 56, 247–250]. However, oxotremorine, RS-86 and the like, which is a nonselective cholinergic agonist for directly stimulating cholinergic receptors, had adverse effects [See; R. Plate et al., Bioorg. Med. Chem., 2000, 8, 449–454].

Muscarinic Acetyl choline receptors exist in central and peripheral nervous systems in five subtype forms and play an important role in brain cognitive function. As the post-synapse muscarinic neuron in the forebrain and hippocampus is known to be relatively unchanging in patients suffering from Alzheimer's disease, research on nootropics and therapeutic agents for Alzheimer's disease focus on developing muscarinic agonists selective for the central nervous system and M1 receptor to decrease adverse effects and increase the efficacy of cholinergic drugs. Recently, muscarinic receptors in post- and pre-synapse of cholinergic nervous system, which is known to play an important role in learning and memorizing, is also found to regulate the process of forming amyloid precursor protein, which plays some role in precipitating beta-amyloid in patients suffering from Alzheimer's disease. Further, muscarinic receptor agonist is known to accelerate secretion of soluble amyloid precursor protein and decrease phosphorylation of tau-protein. Accordingly, to develop nootropics and therapeutic agents for Alzheimer's disease wherein beta-amyloid plaque and nerve fiber entanglement are accumulated, it is important to develop novel muscarinic receptor agonists of muscarinic acetylcholine receptor activity with high medicinal efficacy, low cholinergic adverse effects and selectivity for other receptors [See; C. C. Felder et al., J. Med. Chem. 2000, 43, 23, 4334–4353].

Already known muscarinic agonists active on the central nervous system include Talsaclidin (1997), YM-796 (1990), CI-1017 (2000), Xanomelin (1997), Milameline (1997), Sabcomeline (SB-202026, 1997), Alvameline (LU 25-109, 1997), AF-102 (1997), etc. [See; A. Fisher, Drug Dev. Res. 2000, 50, 291–297]. Additionally, a drug with pyrrolidine ring active on the nervous system includes an agent to ameliorate the condition of Alzheimer's disease such as oxotremorine compounds [See; E. J. Trybulski et al., Bioorg. Med. Chem. Lett. 1992, 2, 827–832] and nootropics [See; D. Manetti et al., J. Med. Chem. 2000, 43, 1969–1974]. Further, although oxadiazole compounds of high affinity and excellent efficacy have been reported, they are known to have adverse effects. Recently, muscarinic agonists such as Pilocarpine (Salagen Tablets, MGI Pharma, Inc., 1998) and Cevimeline (AF102B, EVOXAC™, SnowBrand Pharmaceuticals, Inc., 2000) were approved by FDA as a therapeutic agent for xerostomia originating from Sjogren's syndrome, a sort of autoimmune disease affecting an exocrine gland [See; Drugs of the future, 2000, 25(6), 558–562]. The compound that has activity on muscarinic acetylcholine receptor is useful in pain, glaucoma, schizophrenia, anxiety, manic-depressive psychosis (circular insanity), bipolar psychosis, depression, somnipathy, epilepsy, cerebral ischemia, fecal incontinence and gastrointestinal mobility disorder [See; L. M. Merritt et al., U.S. Pat. No. 5,998,404].

However, some compounds active on muscarinic acetylcholine receptor have adverse effects such as hypersialosis, tears and gastrointestinal disorder. Accordingly, there is still a need to develop a novel compound that has muscarinic acetylcholine receptor activity, high efficacy and low cholinergic adverse effects.

SUMMARY OF THE INVENTION

Thus, the object of the present invention is to provide pyrrolidinone derivatives substituted with azacyclic isoxazole and azacyclic dihydroisoxazole compounds, which have high affinity for muscarinic acetylcholine receptor and thus useful as nootropics and therapeutic agents for neural diseases; and pharmaceutically acceptable salts thereof; processes for the preparation thereof; and pharmaceutical compositions comprising these compounds or salts.

DETAILED DESCRIPTION OF THE PRESENT INVENTION

The present invention provides a compound of formula 1,

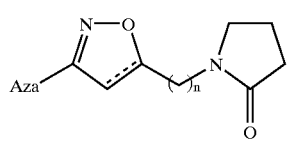

wherein n is 0 or 1; Aza is a heterocycle optionally substituted with $C_{1-4}$ alkyl, or $C_{1-4}$ alkyl substituted with a heterocycle, which represents a saturated or unsaturated five- or six-membered ring having nitrogen(s) as a heteroatom; and a pharmaceutically acceptable salt thereof.

$C_{1-4}$ alkyl as used herein represents straight or branched alkyl group comprising 1 to 4 carbon atoms, such as methyl, ethyl, n-propyl, isopropyl, n-butyl, isobutyl, t-butyl, and more preferably methyl and ethyl.

Heterocycle as used herein represents a saturated or unsaturated five- or six-membered ring having nitrogen(s) as a heteroatom. Preferred heterocycle includes piperidine, pyridine, tetrahydropyridine and pyrrolidinine.

Examples of preferred Aza groups include 1-$C_{1-4}$ alkyl-3-piperidine, 3-pyridine, 1-$C_{1-4}$ alkyl-3-pyridinium salt, 1-$C_{1-4}$ alkyl-3-1,2,5,6-tetrahydropyridine, pyrrolidinyl-N-$C_{1-4}$ alkyl or piperidinyl-N-$C_{1-4}$ alkyl, more preferably, 1-methyl-3-piperidine, 3-pyridine, 1-methyl-3-pyridinium salt, 1-methyl-3-1,2,5,6-tetrahydropyridine, pyrrolidinyl-N-methyl, pyrrolidinyl-N-ethyl, piperidinyl-N-methyl and piperidinyl-ethyl.

Acids to form pharmaceutically acceptable acid addition salt include hydrochloric acid, hydrobromic acid, sulfuric acid, phosphoric acid, acetic acid, benzoic acid, sulfonic acid, fumaric acid, maleic acid, citric acid, lactic acid, tartaric acid, oxalic acid, or smiliar pharmaceutically acceptable organic and inorganic acids.

Examples of preferred compounds of formula 1 of the present invention include 1-[3-(2-piperidin-1-yl-ethyl)-4,5-dihydro-isoxazol-5-yl]-pyrrolidin-2-one, 1-[3-(piperidin-1-yl-methyl-4,5-dihydro-isoxazol-5-yl]-pyrrolidin-2-one, 1-[3-(pyrrolidin-1-yl-methyl)-4,5-dihydro-isoxazol-5-yl]-pyrrolidin-2-one, 1-[3-(2-pyrrolidin-1-yl-ethyl)-4,5-dihydro-isoxazol-5-yl]-pyrrolidin-2-one, 1-[3-(1-methyl-piperidin-3-yl)-4,5-dihydro-isoxazol-5-yl]-pyrrolidin-2-one, 1-(3-pyridin-3-yl-4,5-dihydro-isoxazol-5-yl)-pyrrolidin-2-one, 1-[3-( 1-methyl-1,2,5,6-tetrahydropyridin-3-yl)-4,5-dihydro-isoxazol-5-yl]-pyrrolidin-2-one, 1-[3-(1-methyl-piperidin-3-yl)-4,5-dihydro-isoxazol-5-yl-methyl]-pyrrolidin-2-one, 1-(3-pyridin-3-yl-4,5-dihydro-isoxazol-5-yl-methyl)-pyrrolidin-2-one, 1-[3-(1-methyl-1,2,5,6-tetrahydro-pyridin-3-yl)-4,5-dihydro-isoxazol-5-yl-methyl]-pyrrolidin-2-one, 1-[3-(2-pyrrolidin-1-yl-ethyl)-4,5-dihydro-isoxazol-5-yl-methyl]-pyrrolidin-2-one, 1-(3-pyrrolidin-1-yl-methyl-4,5-dihydro-isoxazol-5-yl-methyl)-pyrrolidin-2-one, 1-[3-(1-methyl-piperidin-3-yl)-isoxazol-5-yl-methyl]-pyrrolidin-2-one, 1-(3-pyridin-3-yl-isoxazol-5-yl-methyl)-pyrrolidin-2-one, or 1-[3-(1-methyl-1,2,5,6-tetrahydro-pyridin-3-yl)-isoxazol-5-yl-methyl]-pyrrolidin-2-one, and pharmaceutically acceptable salts thereof.

Further, the present invention includes the process for the preparation of a compound of formula 1,

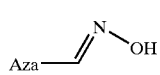

wherein n is 0 or 1; Aza is a heterocycle optionally substituted with $C_{1-4}$ alkyl, or $C_{1-4}$ alkyl substituted with a heterocycle, which represents a saturated or unsaturated five- or six-membered ring having nitrogen(s) as a heteroatom, comprising i) reacting an azacyclic aldehyde oxime of formula 2

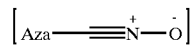

wherein Aza is as defined in the above as starting material to obtain a nitrile oxide of formula 4

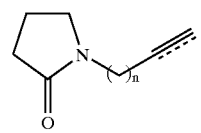

wherein Aza is as defined in the above; and ii) subjecting the resulting compound to a cycloaddition reaction with a pyrrolidinone-containing alkene or alkyne compound of formula 5

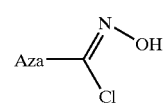

wherein n is as defined in the above.

Below, the process for preparation of substituted pyrrolidinone derivatives of formula 1 of the present invention will be explained in more detail.

Scheme 1

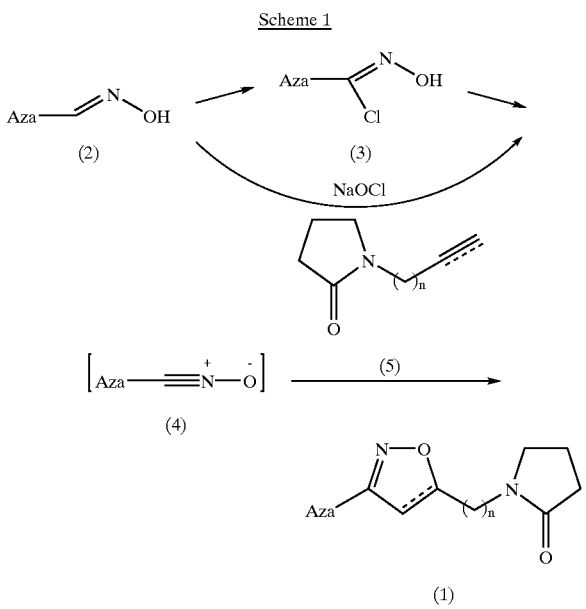

First, the azacyclic aldehyde oxime compound of formula 2 is reacted with Clorax in biphasic solvents of water and organic solvent such as choloroform, methylene chloride, ethyl acetate to obtain the nitrile oxide intermediate of formula 4, which is subjected to a cycloaddition reaction in situ with the alkene or alkyne compound of formula 5 at one step to obtain a compound of formula 1.

Alternatively, the azacyclic aldehyde oxime compound of formula 2 is reacted with N-chlorosuccinimide in a solvent such as tetrahydrofuran, dioxane, ethyl acetate, N,N-dimethylformamide to obtain a hydroxymoyl chloride compound of formula 3 wherein Aza is as defined in the above, which is treated in solvents such as methylene chloride, choloroform, tetrahydrofuran in the presence of a base such as triethylamine to obtain the intermediate of formula 4. It is then subjected to a cycloaddition reaction with the alkene or alkyne compound of formula 5 to obtain a compound of formula 1.

Scheme 2

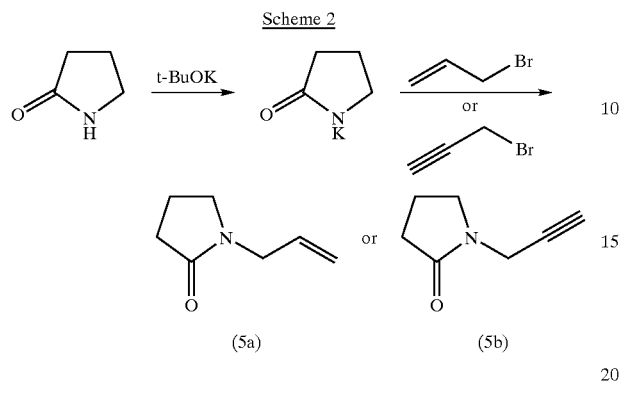

Among compounds of formula 5, N-vinyl pyrrolidinone is commercially available, and the compound of formula 5a or 5b can be prepared by reacting 2-pyrrolidinone with tBuOK in solvents such as tetrahydrofuran, methanol, ethanol or isopropanol, or co-solvents thereof to obtain a potassium salt and then reacting the salt with allyl or propargyl bromide in toluene or benzene solvent, as shown in above scheme 2.

Scheme 3

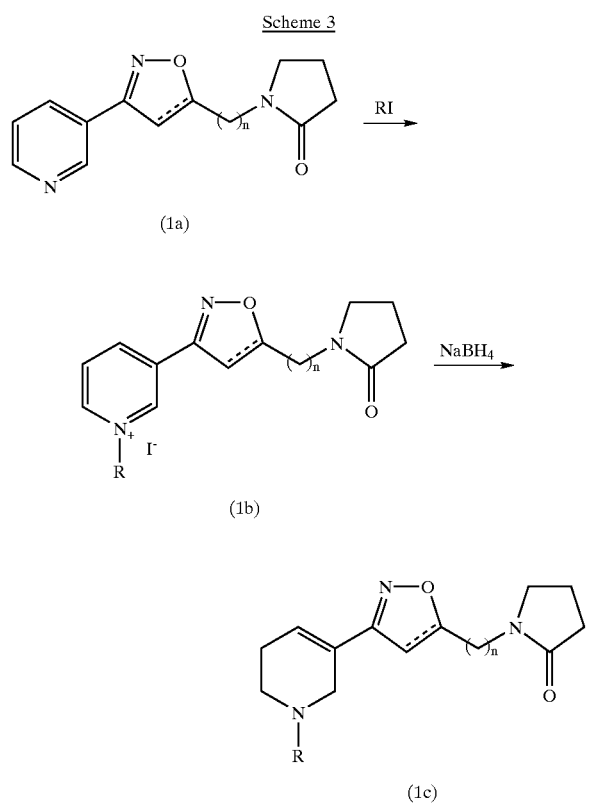

Additionally, a compound of formula 1c, which is the compound of formula 1 wherein Aza is mono-substituted pyridine

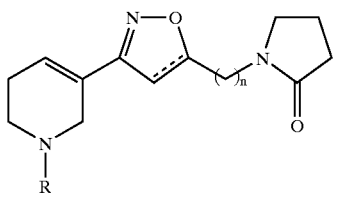

wherein R is $C_{1-4}$ alkyl and n is as defined in the above, can be obtained by reacting a compound of formula 1a, which is the compound of formula 1 wherein Aza is pyridine

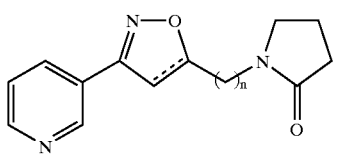

wherein R and n are as defined in the above, with an alkyl iodide to form an alkyl pyridine salt of formula 1b

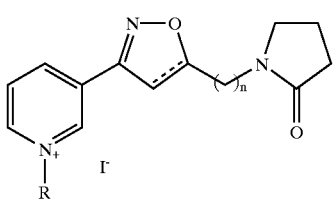

wherein R and n are as defined in the above and then reducing the salt, as shown in above scheme 3.

More specifically, the compound of formula 1a is reacted with the alkyl iodide to obtain the alkyl pyridine salt of formula 1b, which can be recrystallized or concentrated to use at next step. This compound of formula 1b can be reduced with $NaBH_4$ to form the compound of formula 1c.

Free forms of compounds of formula 1 can be converted into an acid addition salt by conventional method of adding a solution containing an appropriate acid in a stoichiometric amount. Pharmaceutically acceptable acid includes hydrochloric acid, hydrobromic acid, sulfuric acid, phosphoric acid, acetic acid, benzoic acid, sulfonic acid, fumaric acid, maleic acid, citric acid, lactic acid, tartaric acid, oxalic acid, or similar pharmaceutically acceptable organic and inorganic acid, and the like.

Additionally, the present invention provides a pharmaceutical composition comprising a compound of formula 1 or its pharmaceutically acceptable acid addition salt as an active ingredient together with a conventional carrier.

The novel compound can be administered orally or parenterally, such as intravenously or intramuscularly, in a typical manner.

The dosage amount may depend on age, condition and weight of a patient, and an administration type. The dosage amount of active ingredient is typically about 0.01 to 200 mg per kg of body weight per day.

The novel compound may be used as a conventional solid or liquid formulations, for example in the form of non-coated or coated tablets (thin film), capsules, powders, granules or solutions. These are prepared in conventional methods. Thus, the active ingredient may be processed together with conventional pharmaceutical adjuvants such as tablet binder, extender, preservative, tablet disintegrant, fluidity controller, plasticizer, wetting agent, dispersing agent, emulsifier, solvent, sustained releasing agent and/or antioxidant.

The compound of the present invention is useful in treating mental disease and cognitive decline originating from abnormality of cholinergic neurotransmission such as Alzheimer's disease. Further, the novel compound of the present invention is useful in pain, glaucoma, psychosis, schizophrenia, anxiety, manic-depressive psychosis (circular insanity), bipolar psychosis, depression, somnipathy, epilepsy, cerebral ischemia, Sjogren's syndrome, fecal incontinence, and gastrointestinal mobility disorder.

The following Examples illustrate the invention in detail but are not intended to limit the scope of the invention in any way.

EXAMPLES

Example 1

Preparation of 3-pyrrolidin-1-yl-propionaldehyde oxime 4 mL (60.2 mmol) of acrolein and 4.85 mL (58.1 mmol) of pyrrolidinone were added in tetrahydrofuran at −15° C., the mixture was reacted for 20 minutes, then 300 mL of solvent mixture of methanol/water (1:2) was added, 4.84 g (1.2 equivalent) of hydroxylamine hydrochloride salt and 3.70 g (0.6 equivalent) of sodium carbonate were added at 0° C., and then the mixture was reacted for 4 hours. After concentrating the solution under reduced pressure, it was washed with brine and water, extracted with chloroform three times, and the resulting organic layer was concentrated under reduced pressure. The concentrated compound was purified by separation with silica gel column chromatography using chloroform/methanol (20:1) as eluent to obtain 4.70 g (55% yield) of the desired compound 3-pyrrolidin-1-yl-propionaldehyde oxime as E/Z (2.1:1) mixture.

$^1$H NMR(CDCl$_3$): δ 7.41 (t, J=5.84, 1H of Z-isomer), 6.75 (t, J=4.99, 1H of E-isomer), 2.8–2.3 (m, 9H), 1.80 (m, 4H); $^{13}$C NMR(CDCl$_3$) for major E-isomer: δ 150.21, 54.24, 52.92, 25.20, 23.71; $^{13}$C NMR(CDCl$_3$) for minor Z-isomer: δ 149.72, 54.32, 53.49, 29.54, 23.68.

Example 2

Preparation of 3-piperidin-1-yl-propionaldehyde oxime 1.2 g (11% yield) of the desired compound 3-piperidin-1-yl-propionaldehyde oxime as E/Z (1.1:1) mixture was prepared from 5 mL (57.13 mmol) of piperidine and 4 mL (60.2 mmol) of acrolein as starting materials by the same preparation method as described in Example 1.

$^1$H NMR(CDCl$_3$): δ 7.42 (t, J=5.83, 1H of E-isomer), 6.78 (t, J=4.86, 1H of Z-isomer), 2.7–2.3 (m, 9H), 1.8–1.3 (m, 6H); $^{13}$C NMR(CDCl$_3$) for major E-isomer: δ 150.62, 56.21, 54,56, 27.48, 25.90, 24.60; $^{13}$C NMR(CDCl$_3$) for minor Z-isomer: δ 150.27, 55.70, 25.95, 24,57, 23.54.

Example 3

Preparation of pyrrolidin-1-yl-acetaldehyde oxime

To 40 mL (0.314 mol) of 50% aqueous solution of chloroacetaldehyde, 80 mL of water was added, 32.8 g (1.5 equivalent) of hydroxylamine hydrochloride salt and 25 g (0.75 equivalent) of sodium carbonate were added, then the mixture was reacted at 0° C. for 2 hours, extracted with diethyl ether three times, washed with brine and concentrated under reduced pressure. The concentrated mixture was distilled under vacuum pump (36° C./0.1 mmHg) to obtain 7.16 g (49% yield) of chloroacetaldehyde oxime.

After dissolving 6.82 g (72.9 mmol) of chloroacetaldehyde oxime in 5 mL of methylene chloride, 12.78 mL (72.9 mmol) of pyrrolidinone dissolved in 50 mL of methylene chloride was added dropwise over 30 minutes. The mixture was reacted at room temperature for 12 hours. After completion of the reaction, the resulting product was concentrated under reduced pressure, 60 mL of Et$_2$O was added, stirred for 30 minutes, upper layer (Et$_2$O) was taken, and then lower layer was again extracted with Et$_2$O. After washing with brine and water, it was kugelrohr-distilled (0.01 mmHg) at a bath temperature set from 80 to 110° C. to obtain 7.29 g (78% yield) of the desired compound pyrrolidin-1-yl-acetaldehyde oxime as E/Z (1.5:1) mixture.

$^1$H NMR(CDCl$_3$): δ 7.52 (t, J=5.98, 1H of major E-isomer), 6.92 (t, J=4.13, 1H of minor Z-isomer), 3.48 (d, 4.14, 2H of minor Z-isomer), 3.26 (d, J=5.99, 2H of major E-isomer), 2.61 (m, 4H), 1.82 (m, 5H); $^{13}$C NMR(CDCl$_3$) for major E-isomer: δ 149.13, 54.61, 54.27, 23.80; $^{13}$C NMR(CDCl$_3$) for minor Z-isomer: δ 149.59, 54.61, 51.19, 23.91.

Example 4

Preparation of piperidin-1-yl-acetaldehyde oxime 5.06 g (54.1 mmol) of chloroacetaldehyde oxime prepared in Example 3 and 9.95 mL (103.9 mmol) of piperidine were reacted by the same method as Example 3. After completion of the reaction, it was filtered and the filtrate layer was collected. A saturated solution of sodium carbonate was added to the residue, extracted with methylene chloride, concentrated under reduced pressure and then solidified with Et$_2$O and hexane. The concentrate layer was purified by separation with silica gel column chromatography using chloroform/methanol (gradient of 30:1 to 20:1) as eluent to obtain 5.5 g (72% yield) of the desired compound piperidin-1-yl-acetaldehyde oxime as E/Z (>10:1) mixture.

$^1$H NMR(CDCl$_3$): δ 7.49 (t, J=6.24, 1H of major E-isomer), 6.89 (t, J=3.93, 1H of minor Z-isomer), 3.33 (br. s, 1H), 3.10 (d, J=6.18, 2H of major E-isomer), 2.45 (m, 4H), 1.61 (m, 4H), 1.47 (m, 2H); $^{13}$C NMR(CDCl$_3$) for major E-isomer: δ 148.23, 57.60, 54.65, 25.60, 24.02.

Example 5

Preparation of 1-methyl-piperidin-3-carbaldehyde oxime

After dissolving 3.0 g (17.5 mmol) of ethyl-1-methyl nipecotate in 18 mL of toluene, 26.9 mL (2.3 equivalent) of DIBAL (25 wt % in toluene) was added dropwise at −78° C. over 0.5 to about 1 hour. After reacting at −78° C. for 1 hour, 5 mL of acetic acid was added, and 15 mL of ethyl acetate was added. The mixture was reacted while warming up slowly to room temperature. A small amount of 10% NaOH was added, then the solution was extracted with ethyl acetate twice, and the aqueous layer was extracted with chloroform three times. The organic layers were combined together, dried over Na$_2$SO$_4$, filtered and concentrated under reduced pressure to obtain 1-methyl-piperidin-3-carbaldehyde. After dissolving this compound in methanol/distilled water (2:1), 1.5 equivalent of hydroxylamine hydrochloride salt and 0.75 equivalent of sodium carbonate were added at 0° C., then the mixture was reacted for 1 hour, concentrated under reduced pressure to remove methanol, a further small amount of water was added. The mixture was extracted with chloroform three times, then dried over $Na_2SO_4$, filtered and concentrated under reduced pressure. The concentrate was purified by separation with silica gel column chromatography using chloroform/methanol (gradient of 10:1 to 7:1) as eluent to obtain 1.38 g (second step, 55% yield) of the desired compound 1-methyl-piperidin-3-carbaldehyde oxime as E/Z (4.34:1) mixture.

$^1$H NMR(CDCl$_3$): δ 7.29 (t, J=5.69, 1H of major E-isomer), 6.53 (t, J=6.75, 1H of minor Z-isomer), 3.0–2.4 (m, 2H), 2.29 (s, 3H), 2.0–1.5 (m, 5H), 1.20 (m, 1H); $^{13}$C NMR(CDCl$_3$) for major E-isomer: δ 152.83, 153.30 (minor Z-isomer), 58.98, 55.95, 46.70, 37.33, 28.04, 24.79.

Example 6

Preparation of 1-allyl pyrrolidin-2-one

After dissolving 35.05 g (0.418 mol) of 2-pyrrolidinone in tetrahydrofuran, 26 g (0.394 mol) of t-BuOK was added, the mixture was reacted for 3 hours, then concentrated under reduced pressure, toluene was added, the mixture was concentrated under reduced pressure (repeatedly twice to three times) to completely remove t-butanol. After adding dropwise 33.85 mL (1 equivalent) of allyl bromide under toluene solution at 40° C. over 1 hour, the mixture was reacted at 67° C. for 30 minutes. After completion of the reaction, it was filtered and distilled in vacuo (66~68° C./0.1 mmHg) to obtain 15.61 g (32% yield) of the desired compound 1-allyl pyrrolidin-2-one.

$^1$H NMR(CDCl$_3$): δ 5.72 (M, 1H), 5.3–5.1 (m, 2H), 3.90 (d, J=6.03, 2H), 3.36 (t, J=7.04, 2H), 2.42 (t, J=7.92, 2H), 2.05 (m, 2H); $^{13}$C NMR(CDCl$_3$): δ 175.17, 132.86, 118.18, 47,12, 45.59, 31.39, 18.17.

Example 7

Preparation of 1-propargyl pyrrolidin-2-one

As in Example 6, 15 g (0.18 mol) of 2-pyrrolidinone and 18.65 mL (1 equivalent) of propargyl bromide were reacted, then distilled in vacuo (66~71° C./0.1 mmHg) to obtain 11.94 g (58% yield) of 1-propargyl pyrrolidin-2-one.

$^1$H NMR(CDCl$_3$): δ 4.11 (d, J=2.48, 2H), 3.50 (t, J=7.03, 2H), 2.41 (t, J=7.92, 2H), 2.23 (t, J=2.51, 1H), 2.07 (m, 2H); $^{13}$C NMR(CDCl$_3$): δ 173.41, 73.84, 46.68, 42.15, 32.25, 31.03, 17.95.

Example 8

Preparation of 1-[3-(2-piperidin-1-yl-ethyl)-4,5-dihydro-isoxazol-5-yl]-pyrrolidin-2-one To a solution of 646 μL (1.5 equivalent) of N-vinyl-pyrrolidin-2-one in 5 mL of chloroform, a biphasic solution of 7.4 mL (3.2 equivalents) of 13% Clorax (NaOCl) and a solution of 629.3 mg (4.03 mmol) of 3-piperidin-1-yl-propionaldehyde oxime compound prepared in Example 2 in 5 mL of chloroform were added slowly over 15 minutes with cooling to 0° C. and stirring vigorously. After reacting at room temperature overnight, the reaction mixture was extracted with chloroform three times, washed with a saturated aqueous solution of sodium carbonate twice following water once, dried over sodium sulfate, filtered and then concentrated under reduced pressure. The concentrate was purified by separation with silica gel column chromatography using chloroform/methanol (30:1) as eluent to obtain 477.4 mg (45% yield) of 1-[3-(2-piperidin-1-yl-ethyl)-4,5-dihydro-isoxazol-5-yl]-pyrrolidin-2-one. Subsequently, 1:1 acid addition salt with oxalic acid was obtained from the diethyl ether solution.

$^1$H NMR(CDCl$_3$): δ 6.47 (dd, J=3.12, 9.83, 1H), 3.37–3.28 (m, 2H), 3.18 (dd, J=9.87, 17.80, 1H), 2.81 (dd, J=3.11, 17.88, 1H), 2.70–2.37 (m, 10H), 2.06–1.93 (m, 2H), 1.58–1.44 (m, 6H); MS(m/e): 181(M$^{30}$ -84), 110, 98, 69, 55.

Example 9

Preparation of 1-[3-(piperidin-1-yl-methyl)-4,5-dihydro-isoxazol-5-yl]-pyrrolidin-2-one The desired compound was prepared by the method of Example 8 from 500 mg (3.52 mmol) of piperidin-1-yl-acetaldehyde oxime prepared in Example 4, and purified by separation with silica gel column chromatography using chloroform/methanol (20:1) to obtain 75.6 mg (9% yield) of 1-[3-(piperidin-1-yl-methyl)-4,5-dihydro-isoxazol-5-yl]-pyrrolidin-2-one. Subsequently, 1:1 acid addition salt with oxalic acid was obtained from the diethyl ether solution.

$^1$H NMR(CDCl$_3$): δ 8 6.49 (dd, J=3.46, 10.04, 1H), 3.33–3.16 (m, 5H), 2.89 (dd, J=3.52, 18.43, 1H), 2.43–2.38 (m, 7H), 2.05–2.01 (m, 2H), 1.59–1.25(m, 7H).

Example 10

Preparation of 1-[3-(pyrrolidin-1-yl-methyl)-4,5-dihydro-isoxazol-5-yl]-pyrrolidin-2-one To a solution of 504.1 mg (3.93 mmol) of pyrrolidin-1-yl-acetaldehyde oxime prepared in Example 3 in 5 mL of tetrahydrofuran, 578 mg (1.1 equivalent) of N-chlorosuccinimide (NCS) was added, and then the mixture was reacted at 50° C. for 1 hour. To this solution, a solution of 630 μL (1.5 equivalent) of N-vinyl pyrrolidin-2-one in 30 mL of toluene was added, and 630 μL (1.1 equivalent) of triethylamine was added. After completion of the reaction, chloroform and a saturated aqueous solution of sodium carbonate were added, the mixture was extracted with chloroform three times, washed with a saturated aqueous solution of sodium carbonate twice following water once, dried over sodium sulfate, filtered and then concentrated under reduced pressure. The dried compound was purified by separation with silica gel column chromatography using chloroform/methanol (gradient of 30:1 to 20:1) as eluent to obtain 102.2 mg (11% yield) of 1-[3-(pyrrolidin-1-yl-methyl)-4,5-dihydro-isoxazol-5-yl]-pyrrolidin-2-one. Subsequently, 1:1 acid addition salt with oxalic acid was obtained from the diethyl ether solution.

$^1$H NMR(CDCl$_3$): δ 6.51 (dd, J=3.72, 10.05, 1H), 3.41 (s, 2H), 3.38–3.17 (m, 4H), 2.89 (dd, J=3.71, 18.33, 1H), 2.60–2.54 (m, 4H), 2.41 (t, J=8.12, 2H), 2.10–1.93 (m, 2H), 1.83–1.79 (m, 3H).

Example 11

Preparation of 1-[3-(2-pyrrolidin-1-yl-ethyl)-4,5-dihydro-isoxazol-5-yl]-pyrrolidin-2-one The desired compound was prepared by the method of Example 8 from 500 mg (3.52 mmol) of 3-pyrrolidin-1-yl-propionaldehyde oxime prepared in Example 1, and purified by separation with silica gel column chromatography using chloroform/methanol (gradient of 20:1 to 10:1) to obtain 117.2 mg (13% yield) of 1-[3-(2-pyrrolidin-1-yl-ethyl)-4,5- dihydro-isoxazol-5-yl]-pyrrolidin-2-one. Subsequently, 1:1 acid addition salt with oxalic acid was obtained from the diethyl ether solution.

$^1$H NMR(CDCl$_3$): δ 6.46 (dd, J=2.98, 9.75, 1H), 3.30 (t, J=7.48, 2H), 3.20 (dd, J=9.77, 17.85, 1H), 2.85–2.53 (m, 9H), 2.39 (t, J=8.31, 2H), 2.08–1.89 (m, 2H), 1.78–1.72 (m, 4H).

Example 12

Preparation of 1-[3-(1-methyl-piperidin-3-yl)-4,5-dihydro-isoxazol-5-yl]-pyrrolidin-2-one The desired compound was prepared by the method of Example 8 from 400 mg (2.81 mmol) of 1-methyl-piperidin-3-carbaldehyde oxime prepared in Example 5, and purified by separation with silica gel column chromatography using chloroform/methanol (gradient of 20:1 to 10:1) as eluent to obtain 216.5 mg (31% yield) of 1-[3-(1-methyl-piperidin-3-yl)-4,5dihydro-isoxazol-5-yl]-pyrrolidin-2-one. Subsequently, 1:1 acid addition salt with oxalic acid was obtained from the diethyl ether solution.

$^1$H NMR(CDCl$_3$): δ 6.45 (dd, J=2.31, 9.66, 1H), 3.32–3.27 (m, 1H), 3.22–3.16 (m, 2H), 2.98–2.68 (m, 4H), 2.40 (t, J=8.17, 2H), 2.30 (s, 3H), 2.09–1.64 (m, 7H), 1.39–1.35 (m, 1H).

Example 13

Preparation of 3-pyridine hydroxymoyl chloride

After dissolving 7 g of 3-pyridin-carboxime in 100 mL of tetrahydrofuran, 8.42 g (1.1 equivalent) of N-chlorosuccinimide was added, and then the mixture was reacted at 50° C. for 1 hour. After completion of the reaction, the reaction was extracted with ethylacetate three times, dried over anhydrous sodium sulfate, filtered and then concentrated under reduced pressure to obtain 11.4 g of 3-pyridine hydroxymoyl chloride quantitatively.

Example 14

Preparation of 1-(3-pyridin-3-yl-4,5-dihydro-isoxazol-5-yl)-pyrrolidin-2-one 2.23 g (12.82 mmol) of 3-pyridine hydroxymoyl chloride prepared by the method of Example 13 was dissolved in 10 mL of methylene chloride, 2.74 mL (2 equivalents) of N-vinyl-2-pyrrolidinone and 2.32 mL (1.2 equivalent) of triethylamine were added, and the mixture was reacted at room temperature for 1 hour. After completion of the reaction, the reaction was extracted with chloroform three times, washed with a saturated aqueous solution of sodium carbonate twice following water once, dried over sodium sulfate, filtered and then concentrated under reduced pressure. The dried compound was purified by separation with silica gel column chromatography using chloroform/methanol (gradient of 30:1 to 15:1) as eluent to obtain 2.16 g (73% yield) of 1-(3-pyridin-3-yl-4,5-dihydro-isoxazol-5-yl)-pyrrolidin-2-one.

$^1$H NMR(CDCl$_3$): δ 8.84–7.37 (m, 4H), 6.70 (dd, J=3.63, 9.96, 1H), 3.24–3.16 (m, 1H), 2.46–2.41 (m, 2H), 2.09–1.81 (m, 2H); MS(m/e): 231(M$^+$), 173, 147, 78.

Example 15

Preparation of 1-[3-(1-methyl-1,2,5,6-tetrahydropyridin-3-yl)-4,5-dihydro-isoxazol-5-yl]-pyrrolidin-2-one 1.35 g (5.83 mmol) of 1-(3-pyridin-3-yl-4,5-dihydro-isoxazol-5-yl)-pyrrolidin-2-one from Example 14 was dissolved in 15 mL of acetone, then 1.09 mL (3 equivalents) of methyl iodide was added at 0° C., and the mixture was reacted for 3 hours. After filtering by adding diethyl ether, the resulting residue was dried to obtain 2.05 g (94% yield) of pyridinium iodide salt. 1.84 g of this salt compound was dissolved in 30 mL of ethanol/water (1:1), then 560 mg (3 equivalents) of sodium borohydride was added at 0° C., and the mixture was reacted at 0° C. for 30 minutes. After completion of the reaction, 0.5 mL of acetone was added, the solution was concentrated under reduced pressure to remove the residual acetone and ethanol, water was added to the residue, the solution was extracted with chloroform three times, then washed with brine and water, dried over sodium sulfate, filtered and then concentrated under reduced pressure. The concentrated compound was purified by separation with silica gel column chromatography using chloroform/methanol (gradient of 30:1 to 15:1) as eluent to obtain 902.5 mg (73.4% yield) of the desired compound 1-[3-(1-methyl-1,2,5,6-tetrahydropyridin-3-yl)-4,5-dihydro-isoxazol-5-yl]-pyrrolidin-2-one. Subsequently, 1:1 acid addition salt with oxalic acid was obtained from the diethyl ether solution.

$^1$H NMR(CDCl$_3$): δ 6.46 (dd, J=3.35, 9.80, 1H), 6.30–6.01 (m, 1H), 3.27–3.11 (m, 4H), 2.86–2.83 (m, 1H), 2.52–2.30 (m, 9H), 1.95–1.92 (m, 2H); MS(m/e): 249(M$^+$), 189, 164, 121, 109, 94.

Example 16

Preparation of 1-[3-(1-methyl-piperidin-3-yl)-4,5-dihydro-isoxazol-5-yl-methyl]-pyrrolidin-2-one The desired compound was prepared by the method of Example 8 from 300 mg (2.11 mmol) of 1-methyl-piperidin-3-carbaldehyde oxime prepared in Example 5 and 528 mg (2 equivalents) of 1-allyl pyrrolidin-2-one prepared in Example 6 and purified by separation with silica gel column chromatography using chloroform/methanol (gradient of 20:1 to 10:1) as eluent to obtain 230.1 mg (41% yield) of 1-[3-(1-methyl-piperidin-3-yl)-4,5-dihydro-isoxazol-5-yl-methyl]-pyrrolidin-2-one. Subsequently, 1:1 acid addition salt with oxalic acid was obtained from the diethyl ether solution.

$^1$H NMR(CDCl$_3$): δ 4.73–4.69(m, 1H), 3.59–3.39 (m, 4H), 3.01–2.65 (m, 5H), 2.41–2.38 (m, 2H), 2.30 (s, 3H), 2.07–1.25 (m, 8H).

Example 17

Preparation of 1-(3-pyridin-3-yl-4,5-dihydro-isoxazol-5-yl-methyl)-pyrrolidin-2-one The desired compound was prepared by the method of Example 8 from 500 mg (4.09 mmol) of 3-pyridine aldoxime and 1.02 g (2 equivalents) of 1-allyl pyrrolidin-2-one prepared in Example 6, and purified by separation with silica gel column chromatography using ethyl acetate and then chloroform/methanol (30:1) as eluent to obtain 578.4 mg (58% yield) of 1-(3-pyridin-3-yl-4,5-dihydro-isoxazol-5-yl-methyl)-pyrrolidin-2-one.

$^1$H NMR(CDCl$_3$): δ 8.86–7.99 (m, 4H), 5.01–4.96 (m, 1H), 3.68–3.50 (m, 4H), 3,48–3.19 (m, 2H), 2.41–2.34 (m, 2H), 2.03–1.95 (m, 2H); $^{13}$C NMR(CDCl$_3$): δ 176.13, 154,67, 151.16, 147.82, 133.75, 125.37, 80.64, 49.24, 46.14, 37.33, 30.62, 18.34.

Example 18

Preparation of 1-[3-(1-methyl-1,2,5,6-tetrahydro-pyridin-3-yl)-4,5-dihydro-isoxazol-5-yl-methyl]-pyrrolidin-2-one The desired compound was prepared by the method of Example 15 from 524 mg (2.136 mmol) of 1-(3-pyridin-3- yl-4,5-dihydro-isoxazol-5-yl-methyl)-pyrrolidin-2-one prepared in Example 17, and purified by separation with silica gel column chromatography using chloroform/methanol (gradient of 30:1 to 10:1) as eluent to obtain 334.0 mg (65% yield) of the desired compound 1-[3-(1-methyl-1,2,5,6-tetrahydro-pyridin-3-yl)-4,5-dihydro-isoxazol-5-yl-methyl]-pyrrolidin-2-one. Subsequently, 1:1 acid addition salt with oxalic acid was obtained from the diethyl ether solution.

$^1$H NMR(CDCl$_3$): δ 6.06–6.04 (m, 1H), 4.82–4.73 (m, 1H), 3.64–3.43 (m, 4H), 3.27–3.12 (m, 3H), 2.97–2.93 (m, 1H), 2.55–2.49 (m, 1H), 2.41–2.35 (m, 7H), 2.02–1.93 (m, 2H); $^{13}$CNMR(CDCl$_3$): δ 176.38, 157.16, 131.01, 128.42, 80.15, 77.86, 77.43, 77.01, 53.92, 51.69, 49.59, 46.49, 46.13, 37.31, 31.07, 27.10, 18.74.

Example 19

Preparation of 1-[3-(2-pyrrolidin-1-yl-ethyl)-4,5-dihydro-isoxazol-5-yl-methyl]-pyrrolidin-2-one The desired compound was prepared by the method of Example 8 from 400 mg (2.813 mmol) of 3-pyrrolidin-1-yl-propionaldehyde oxime prepared in Example 1 and 704 mg (2 equivalents) of 1-allyl pyrrolidin-2-one prepared in Example 6, and purified by separation with silica gel column chromatography using chloroform/methanol (gradient of 20:1 to 7:1) as eluent to obtain 148 mg (20% yield) of 1-[3-(2-pyrrolidin-1-yl-ethyl)-4,5-dihydro-isoxazol-5-yl-methyl]-pyrrolidin-2-one. Subsequently, 1:1 acid addition salt with oxalic acid was obtained from the diethyl ether solution.

$^1$H NMR(CDCl$_3$): δ 4.75–4.68 (m, 1H), 3.64–3.50 (m, 3H), 3.41–3.37 (m, 1H), 3.11–3.01 (m, 1H), 2.84–2.67 (m, 3H), 2.58–2.53 (m, 6H), 2.41–2.35 (m, 2H), 2.05–2.01 (m, 2H), 1.81 (m, 4H); $^{13}$C NMR(CDCl$_3$): δ 176.24, 158.43, 79.33, 54.32, 54.31, 53.02, 49.52, 46.53, 40.53, 31.11, 27.70, 23.85, 23.84, 18.72.

Example 20

Preparation of 1-(3-pyrrolidin-1-yl-methyl-4,5-dihydro-isoxazol-5-yl-methyl)-pyrrolidin-2-one The desired compound was prepared by the method of Example 8 from 400 mg (3.121 mmol) of pyrrolidin-1-yl-acetaldehyde oxime prepared in Example 3 and 781 mg (2 equivalents) of 1-allyl pyrrolidin-2-one prepared in Example 6, and purified by separation with silica gel column chromatography using chloroform/methanol (gradient of 30:1 to 20:1) as eluent to obtain 30.3 mg (4% yield) of 1-(3-pyrrolidin-1-yl-methyl-4,5-dihydro-isoxazol-5-yl-methyl)-pyrrolidin-2-one. Subsequently, 1:1 acid addition salt with oxalic acid was obtained from the diethyl ether solution.

$^1$H NMR(CDCl$_3$): δ 4.81–4.71 (m, 1H), 3.63–3.53 (m, 3H), 3.36–3.29 (m, 3H), 3.16–2.81 (m, 2H), 2.56–2.51 (m, 4H), 2.41–2.39 (m, 2H), 2.05–2.01 (m, 2H), 1.83–1.76 (m, 4H); $^{13}$C NMR(CDCl$_3$): δ 176.14, 158.49, 79.59, 54.62, 52.62, 49.43, 46.65, 39.80, 31.05, 30.04, 23.99, 23.97, 18.61.

Example 21

Preparation of 1-[3-(1-methyl-piperidin-3-yl)-isoxazol-5-yl-methyl]-pyrrolidin-2-one The desired compound was prepared by the method of Example 8 from 300 mg (2.11 mmol) of 1-methyl-piperidin-3-carbaldehyde oxime prepared in Example 5 and 520 mg (2 equivalents) of 1-propargyl pyrrolidin-2-one prepared in Example 7, and purified by separation with silica gel column chromatography using chloroform/methanol (gradient of 20:1 to 10:1) as eluent to obtain 278.1 mg (50% yield) of 1-[3-(1-methyl-piperidin-3-yl)-isoxazol-5-yl-methyl]-pyrrolidin-2-one. Subsequently, 1:1 acid addition salt with oxalic acid was obtained from the diethyl ether solution.

$^1$H NMR(CDCl$_3$): δ 6.08 (s, 1H), 4,54 (s, 2H), 3.47 (t, J=7.00, 2H), 3.05–2.97 (m, 2H), 2.86–2.83 (m, 1H), 2.42 (t, J=7.90, 2H), 2.31 (s, 3H), 2.11–1.95 (m, 4H), 1.82–1.71 (m, 2H), 1.47–1.42 (m, 1H); $^{13}$C NMR(CDCl$_3$): δ 175.42, 167.67, 166.48, 101.74, 60.29, 56.05, 47.75, 46.89, 38.48, 35.16, 30.80, 29.46, 25.40, 18.24.

Example 22

Preparation of 1-(3-pyridin-3-yl-isoxazol-5-yl-methyl)-pyrrolidin-2-one

The desired compound was prepared by the method of Example 8 from 500 mg (4.09 mmol) of 3-pyridine aldoxime and 1.0 g (2 equivalents) of 1-propargyl pyrrolidin-2-one prepared in Example 7, and purified by separation with silica gel column chromatography using ethyl acetate and then chloroform/methanol (30:1) to obtain 352.2 mg (35.4% yield) of 1-(3-pyridin-3-yl-isoxazol-5-yl-methyl)-pyrrolidin-2-one.

$^1$H NMR(CDCl$_3$): δ 9.01–7.39 (m, 4H), 6.59 (s, 1H), 4.66 (s, 2H), 3.52 (t, J=7.02, 2H), 2.4 (t, J=7.94, 2H), 2.15–2.05 (m, 2H); $^{13}$C NMR(CDCl$_3$): δ 175.16, 168.95, 160.19, 151.17, 147.93, 134.04, 124.94, 123.82, 100.67, 47.39, 38.17, 30.37, 17.85.

Example 23

Preparation of 1-[3-(1-methyl-1,2,5,6-tetrahydro-pyridin-3-yl)-isoxazol-5-yl-methyl]-pyrrolidin-2-one The desired compound was prepared by the method of Example 15 from 303.2 mg (1.246 mmol) of 1-(3-pyridin-3-yl-isoxazol-5-yl-methyl)-pyrrolidin-2-one prepared in Example 22, and purified by separation with silica gel column chromatography using chloroform/methanol (gradient of 30:1 to 10:1) as eluent to obtain 138.1 mg (53% yield) of the desired compound 1-[3-(1-methyl-1,2,5,6-tetrahydro-pyridin-3-yl)-isoxazol-5-yl-methyl]-pyrrolidin-2-one. Subsequently, 1:1 acid addition salt with oxalic acid was obtained from the diethyl ether solution.

$^1$H NMR(CDCl$_3$): δ 6.37–6.32 (m, 1H), 6.28 (s, 1H), 4,55 (s, 2H), 3.46 (t, J=7.02, 2H), 3.36–3.31 (m, 2H), 2.58 (t, J=5.70, 2H), 2.44–2.31 (m, 7H), 2.17–2.01 (m, 2H); $^{13}$C NMR(CDCl$_3$): δ 170.02, 167.08, 161.94, 128.50, 126.72, 99.54, 53.87, 51.29, 47.31, 45.75, 38.05, 30.42, 26.50, 17.82.

Measurement of Drug Effect

In order to demonstrate the availability of the desired compounds of formula 1 according to the present invention, the activity of the representative compounds as muscarinic acetylcholine receptor agonists was examined.

The efficacy of novel anti-dementia candidate substances acting on muscarinic receptors is demonstrated by primarily investigating the affinity of the substances for the receptors using the muscarinic receptor affinity screening test, and then analyzing the function of the substances (a muscarinic agonist/antagonist) by [$^3$H]-oxotremorine affinity screening test, the organ bath method using avulsed ileum of Guinea pig, and phosphoinositide turnover measurement. The candidate substances thus screened are finally accessed for their efficacy using passive avoidance test, which is in vivo test on learning and memorizing, and general pharmacological/behavioral measurements, and the like.

In Vitro Affinity Screening Test to Screen Muscarinic Receptor Agonist

[$^3$H]-N-methyl-scopolamine ([$^3$H]-NMS) Affinity Screening Test

In order to exclude the interaction between subtypes, human recombinant muscarinic receptor subtypes 1, 2 and 3 expressed in CHO cells (M1, M2 and M3, Biosignal, Canada) were purchased and used as receptor sources. [$^3$H]-N-methyl-scopolamine (NEN, NET-636) was used as radioisotope labeled ligands, and atropine was used for the measurement of the non-specific binding ability. About 10 kinds of experimental apparatuses including Liquid Scintillation Counter (MicroBeta 1450 plus), Inotech cell harvester (96-well) were used.

In order to determine the effect of each compound on M1 and M2 receptors, the compounds were reacted with the receptors using radioisotope labeled ligands. After the reaction, the excess unbound ligands were removed by filtering with a glass fiber filter. The amount of radioisotopes remaining on the washed filter plate was then measured to quantify the binding reaction between the receptors and the ligands and, from the results, the affinity of the drugs for the receptors was determined.

The freeze-stored receptors at −70° C. were suspended in test buffer solutions and then the screening test (BioRad protein) was carried out to determine the optimum concentration of the proteins. Thereafter, 50 µL of hot-ligands and 10 µL of test drugs were added to 96-well plate and 100 µL of 50 mM TRIS buffer (pH 7.2) containing 10 mM MgCl$_2$ and 1 mM EDTA was added as a test buffer. The final volume of the reaction was 0.25 mL. The reaction was initiated by adding 100 µL of the diluted receptor suspension, and continued for 60 minutes on a shaking incubator at 27° C. This test for the test drugs was repeated four times. After 60 minutes, the reaction was terminated by adding cold TRIS buffer (0.5 mL, pH 7.4). The excess unbound radioisotopes were removed from the reaction mixture using Inotech cell harvester system. After washing the mixture, the radioactivity detected by the filter mat was measured using Liquid Scintillation Counter. As primary stage of the efficacy screening, the drugs at two concentrations (1 µM, 10 µM) were screened for their affinity for the receptors. As secondary stage, the drugs showing remarkable efficacies were determined at the lower concentrations. Finally, IC$_{50}$ values were calculated at the gradient of 10 concentrations. The test drugs were diluted sequentially for the required concentrations by dissolving them in dimethylsulfoxide (DMSO). The final reaction concentration 1% of dimethylsulfoxide did not affect the binding reaction. From the saturation affinity screening test, K$_d$ and B$_{max}$ values, and IC$_{50}$ or K$_i$ values of each test drugs were calculated by observing the non-linear regression using prism (Graphpad software Inc.,USA).

In the equilibrium affinity screening test, [$^3$H]-N-methyl-scopolamines at the gradient of 12 concentrations were used for the measurement of the binding ability (IC$_{50}$). In the competition screening test, 1 nM of [$^3$H]-N-methyl-scopolamines, and the reference drugs at the gradient of 10 concentrations were used for the measurement. 4-DAMP-methyliodide, Pirenzepine, p-F-hexahydro-sila-defenidol, Methoctramine, and the like were used as the reference drugs.

[$^3$H]-oxotremorine-M ([$^3$H]-Oxo-M) Affinity Screening Test

The experimental principle was the same as [$^3$H]-NMS affinity screening test. The present experiment was carried out in order to identify the pharmacological functions (an agonist or antagonist) of the compounds showing high affinity in [3H]-NMS affinity screening test. The functions of the compounds may be determined by carrying out both of [$^3$H]-NMS and [$^3$H]-Oxo-M (oxotremorine) affinity screening tests to measure their respective IC$_{50}$ values and calculating ratios (NMS/Oxo-M) of the measured IC$_{50}$ values. Generally, the compounds are evaluated as muscarinic receptor full agonists when the ratio is greater than 180, as partial agonists when the ratio is from 14 to 130, and as antagonists when the ratio is from 0.2 to 1.9.

Preparation of Brain Membrane

Synapse membranes for binding assay of Oxo-M binding receptor of muscarinic receptors were directly prepared and used in the laboratory as follows: male Sprague-Dawley rats (supplied from Laboratory Animal Center of Korea Research Institute of Chemical Technology, 250 to 300 g) were sacrificed by decapitation. The brain tissues were immediately removed and the forebrain was obtained, which was sectioned into small pieces. After adding 10-fold amount of ice-cooled solution of sucrose (0.32M), the sectioned forebrain was homogenized using Teflon-glass homogenizer (Contorque, Eberbach) at 10 strokes and 500 rpm, centrifuged at 1000 g for 15 minutes, and then the supernatant was again centrifuged at 17000 g for 20 minutes. The pellet was stored at −20° C. and then used.

Before the pellet was used at this assay, it was suspended in 10 mL of 20 M HEPES buffer (pH 7.4), again centrifuged at 17000 g for 15 minutes and then washed. Finally, the washed membrane was diluted in ice-cooled 20 mM HEPES buffer (pH 7.4) to the final concentration of 1:100 (wet wt/v) and used at this assay. All test samples were tested four times, and 20 mM HEPES buffer (pH 7.4) was used as a buffer for screening test. The final volume of reaction was 1 mL, and 24-well plate (costar 24-well) was used. 50 µL of hot-ligand (Oxo-M 5 nM) and 10 µL of test drugs were included therein, and the reaction was initiated by adding 750 µL of synapse membrane and continued at 30° C. for 40 minutes on the shaking incubator. 2 µM atropine was used for non-specific binding in all tests. After completion of the reaction, the receptor binding ligands and non-binding ligands were separated by using Inotech cell harvester (24-channels, Inotech, Switzerland) and filtering under reduced pressure (10×ice-cooled saline) with Wallac GF/C filter (pre-immersed in 0.05% polyethylene imine). The radioactivity of the receptor binding ligands was detected by Liquid Scintillation Counter (MicroBeta Plus, Wallac, Finland).

The test drugs were diluted sequentially for the required concentrations by dissolving them in dimethylsulfoxide (DMSO) and used in the test. The final reaction concentration 1% of DMSO did not affect the binding reaction. From the saturated affinity screening test, K$_d$ and B$_{max}$ values, and IC$_{50}$ or K$_i$ values of respective test drugs were calculated by observing the non-linear regression using prism (Graphpad software Inc., USA). The saturated affinity screening test was carried out in the range of 0.1 to 10 nM of [$^3$H]-Oxo-M ligand as described above.

The following table 1 illustrates the affinity of representative compounds of the present invention for muscarinic receptors measured by binding of [$^3$H]-N-methyl scopolamine ([$^3$H]-NMS) and [$^3$H]-oxotremorine ([$^3$H]-Oxo-M) to cortex receptor of rats. The affinity was expressed as IC$_{50}$ that is the concentration of the substrate compound to inhibit 50% of the specific binding of [$^3$H]-NMS and [$^3$H]-Oxo-M to the receptor, and compared with arecoline as a reference compound.

TABLE 1

Affinity of Representative Compounds for Muscarinic Receptors

| Compound | [$^3$H]—NMS IC$_{50}$ ($\mu$M) | [$^3$H]-Oxo-M IC$_{50}$ ($\mu$M) |
|---|---|---|
| Example 15 | 8.31 | 0.22 |
| Example 18 | 0.18 | 0.03 |
| Example 23 | 1.49 | 0.37 |
| Arecoline | 87.1 | 0.14 |

As shown in Table 1, the novel compounds according to the invention showed high affinity for muscarinic receptors. The compounds also showed to have higher efficacies and effects as partial agonists which was determined by the ratio between the inhibition of the compounds to N-methyl scopolamine (NMS) and the inhibition of the compounds to oxotremorine (Oxo-M).

What is claimed is:

1. A substituted pyrrolidinone compound of formula 1,

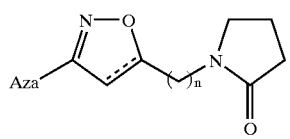

1 wherein n is 0 or 1; Aza is a heterocycle optionally substituted with C$_{1-4}$ alkyl, or C$_{1-4}$ alkyl substituted with a heterocycle, which represents a saturated or unsaturated five- or six-membered ring having one nitrogen as a heteroatom; and a pharmaceutically acceptable salt thereof.

2. The compound of the formula 1 according to claim 1, wherein Aza is 1-methyl-3-piperidine, 3-pyridine, 1-methyl-3-pyridinium salt, 1-methyl-3-1,2,5,6-tetrahydropyridine, pyrrolidinyl-N-methyl, pyrrolidinyl-N-ethyl, piperidinyl-N-methyl or piperidinyl-N-ethyl.

3. The compound of the formula 1 according to claim 1, selected from:
   1-[3-(2-piperidin-1-yl-ethyl)-4,5-dihydro-isoxazol-5-yl]-pyrrolidin-2-one,
   1-[3-(piperidin-1-yl-methyl)-4,5-dihydro-isoxazol-5-yl]-pyrrolidin-2-one
   1-[3-(pyrrolidin-1-yl-methyl)-4,5-dihydro-isoxazol-5-yl]-pyrrolidin-2-one
   1-[3-(2-pyrrolidin-1-yl-ethyl)-4,5-dihydro-isoxazol-5-yl]-pyrrolidin-2-one,
   1-[3-(1-methyl-piperidin-3-yl)-4,5-dihydro-isoxazol-5-yl]-pyrrolidin-2-one,
   1-(3-pyridin-3-yl-4,5-dihydro-isoxazol-5-yl)-pyrrolidin-2-one,
   1-[3-(1-methyl-1,2,5,6-tetrahydropyridin-3-yl)-4,5-dihydro-isoxazol-5-yl]-pyrrolidin-2-one,
   1-[3-(1-methyl-piperidin-3-yl)-4,5-dihydro-isoxazol-5-yl-methyl]-pyrrolidin-2-one,
   1-(3-pyridin-3-yl-4,5-dihydro-isoxazol-5-yl-methyl)-pyrrolidin-2-one,
   1-[3-(1-methyl-1,2,5,6-tetrahydro-pyridin-3-yl)-4,5-dihydro-isoxazol-5-yl-methyl]-pyrrolidin-2-one,
   1-[3-(2-pyrrolidin-1-yl-ethyl)-4,5-dihydro-isoxazol-5-yl-methyl]-pyrrolidin-2-one
   1-(3-pyrrolidin-1-yl-methyl-4,5-dihydro-isoxazol-5-yl-methyl)-pyrrolidin-2-one,
   1-[3-(1-methyl-piperidin-3-yl)-isoxazol-5-yl-methyl]-pyrrolidin-2-one,
   1-(3-pyridin-3-yl-isoxazol-5-yl-methyl)-pyrrolidin-2-one, or
   1-[3-(1-methyl-1,2,5,6-tetrahydro-pyridin-3-yl)-isoxazol-5-yl-methyl]-pyrrolidin-2-one, and
pharmaceutically acceptable salts thereof.

4. A process for the preparation of a compound of formula 1,

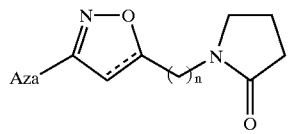

1 wherein n is 0 or 1; Aza is a heterocycle optionally substituted with C$_{1-4}$ alkyl, or C$_{1-4}$ alkyl substituted with a heterocycle, which represents a saturated or unsaturated five- or six-membered ring having one nitrogen as a heteroatom, comprising
   i) reacting an azacyclic aldehyde oxime of formula 2

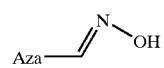

2 wherein Aza is as defined in the above, as a starting material to obtain a nitrile oxide of formula 4

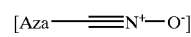

4 wherein Aza is as defined in the above; and
   ii) subjecting the resulting compound to a cycloaddition reaction with a pyrrolidinone-containing alkene or alkyne compound of formula 5

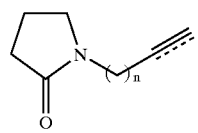

5 wherein n is as defined in the above.

5. The process according to claim 4, wherein the nitrile oxide of formula 4 is obtained by reacting the azacyclic aldehyde oxime compound of formula 2 with Clorax.

6. The process according to claim 4, wherein the nitrile oxide of formula 4 is obtained via a hydroxymoyl chloride compound of formula 3

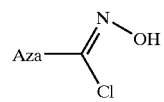

3 wherein Aza is as defined in claim 1, obtained by reacting the azacyclic aldehyde oxime compound of formula 2 with N-chlorosuccinimide.

7. The process according to claim 4, wherein a compound of formula 1c, which is the compound of formula 1 wherein Aza is mono-substituted pyridine

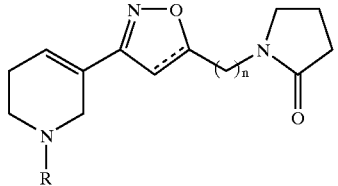

1c wherein R is $C_{1-4}$ alkyl, and n is as defined in claim 1, is obtained by reacting a compound of formula 1a, which is the compound of formula 1 wherein Aza is pyridine

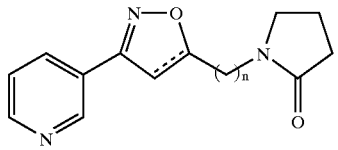

1a wherein n is as defined in the above, with an alkyl iodide to form an alkyl pyridine salt of formula 1b

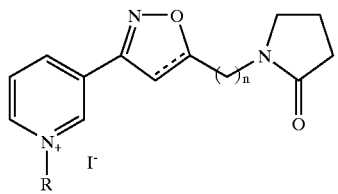

1b wherein R and n is as defined in the above and then reducing the salt.

8. A pharmaceutical composition, which comprises a compound of formula 1 according to claim 1 as an active ingredient, and a pharmaceutically acceptable carrier.

9. A pharmaceutical composition which comprises a compound of formula 1 according to claim 2 as an active ingredient and a pharmaceutically acceptable carrier.

10. A pharmaceutical composition which comprises a compound of formula 1 according to claim 3 as an active ingredient and a pharmaceutically acceptable carrier.

11. A pharmaceutical composition, which comprises a pharmaceutically acceptable salt of the compound of formula 1 according to claim 1 as an active ingredient, and a pharmaceutically acceptable carrier.

12. A pharmaceutical composition which comprises a pharmaceutically acceptable salt of the compound of formula 1 according to claim 2 as an active ingredient and a pharmaceutically acceptable carrier.

13. A pharmaceutical composition which comprises a pharmaceutically acceptable salt of the compound of formula 1 according to claim 3 as an active ingredient and a pharmaceutically acceptable carrier.

* * * * *